US00PP15642P3

(12) United States Plant Patent
Brljevich et al.

(10) Patent No.: US PP15,642 P3
(45) Date of Patent: Mar. 8, 2005

(54) VARIETY OF CALLA LILY NAMED 'HAWAII'

(50) Latin Name: *Zantedeschia sprengeri*
Varietal Denomination: Hawaii

(75) Inventors: Trevor Brljevich, Maungaturoto (NZ); Yvonne Brljevich, Maungaturoto (NZ)

(73) Assignee: Pukekaroro Exotics Ltd., Paparoa (NZ)

( * ) Notice: Subject to any disclaimer, the term of this patent is extended or adjusted under 35 U.S.C. 154(b) by 0 days.

(21) Appl. No.: 10/423,334

(22) Filed: Apr. 25, 2003

(65) Prior Publication Data

US 2004/0216200 P1 Oct. 28, 2004

(51) Int. Cl.[7] ..... A01H 5/00

(52) U.S. Cl. ..... Plt./263

(58) Field of Search ..... Plt./263

(56) References Cited

PUBLICATIONS

GTITM UPOV ROM Citation for 'Hawaii' as per NZ PBR ZAN020; Jun. 26, 2001.*

* cited by examiner

*Primary Examiner*—Kent Bell
*Assistant Examiner*—Louanne Krawczewicz Myers
(74) *Attorney, Agent, or Firm*—Webb Ziesenheim Logsdon Orkin & Hanson, P.C.

(57) ABSTRACT

'Hawaii' is a new variety of calla lily having beautiful multi-colored flowers and strong branching.

2 Drawing Sheets

Botanical classification: *Zantedeschia sprengeri.*
Varietal denomination: 'Hawaii'.

BACKGROUND OF THE NEW PLANT

The present invention comprises a new and distinct cultivar of calla lily, botanically known as *Zantedeschia sprengeri* and hereinafter referred to by the cultivar name 'Hawaii'.

'Hawaii' was discovered in 1997 and chosen from a selection of seedling tubers of unknown parentage in Maungaturoto, New Zealand. The first act of asexual reproduction of 'Hawaii' by tissue culture was performed in 1998 in Auckland, New Zealand. Subsequent asexual reproductions by tissue culture have demonstrated that the combination of characteristics as herein disclosed for the new cultivar are retained through successive generations of asexual reproduction and reproduces true to type.

The following traits have been repeatedly observed and determined to be basic characteristics of 'Hawaii' which, in combination, distinguish this calla lily as a new and distinct cultivar:

1. 'Hawaii' is more nectarine in color than 'Red Sox' (U.S. Plant Pat. No. 14,063);
2. 'Hawaii' has a more rounded and larger spathe than 'Neroli' (unpatented);
3. 'Hawaii' has more scarlet red coloring than 'Hazel Marie' (unpatented), 'Mango' (unpatented), 'Treasure' (unpatented), and 'Hot Shot' (unpatented);
4. 'Hawaii' has a different leaf shape than 'Mango', 'Treasure', and 'Hot Shot'; and
5. The overlapping portion of the spathe of 'Hawaii' is generally incomplete and turning downwards.

BRIEF DESCRIPTION OF THE DRAWINGS

The accompanying photographic drawings illustrate the new variety, with the colors being as nearly true as is possible with color illustrations of this type.

DESCRIPTION OF THE NEW PLANT

Figure 1:
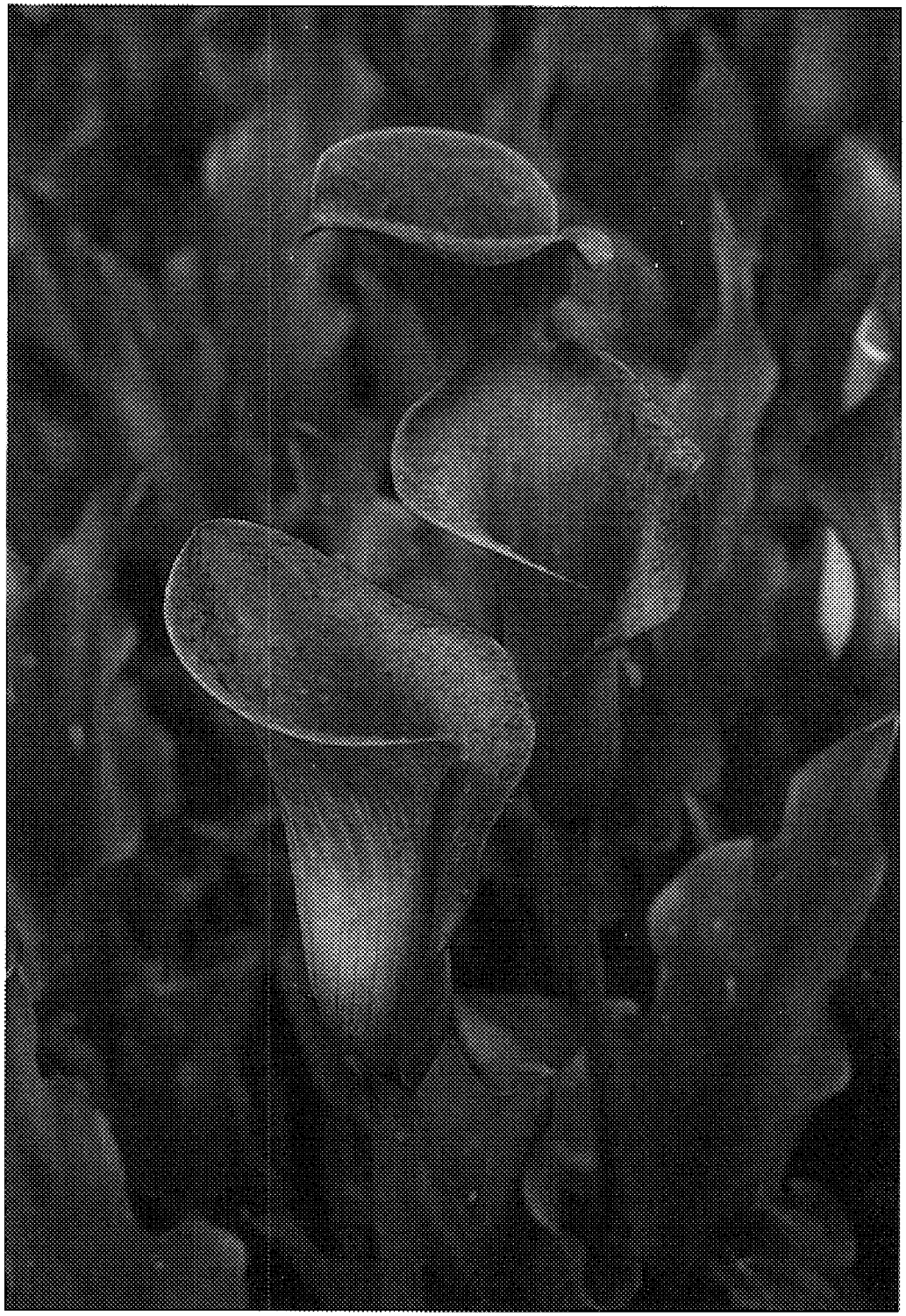
FIG. 1 is a close-up photograph of flowers of the new variety.
Figure 2:
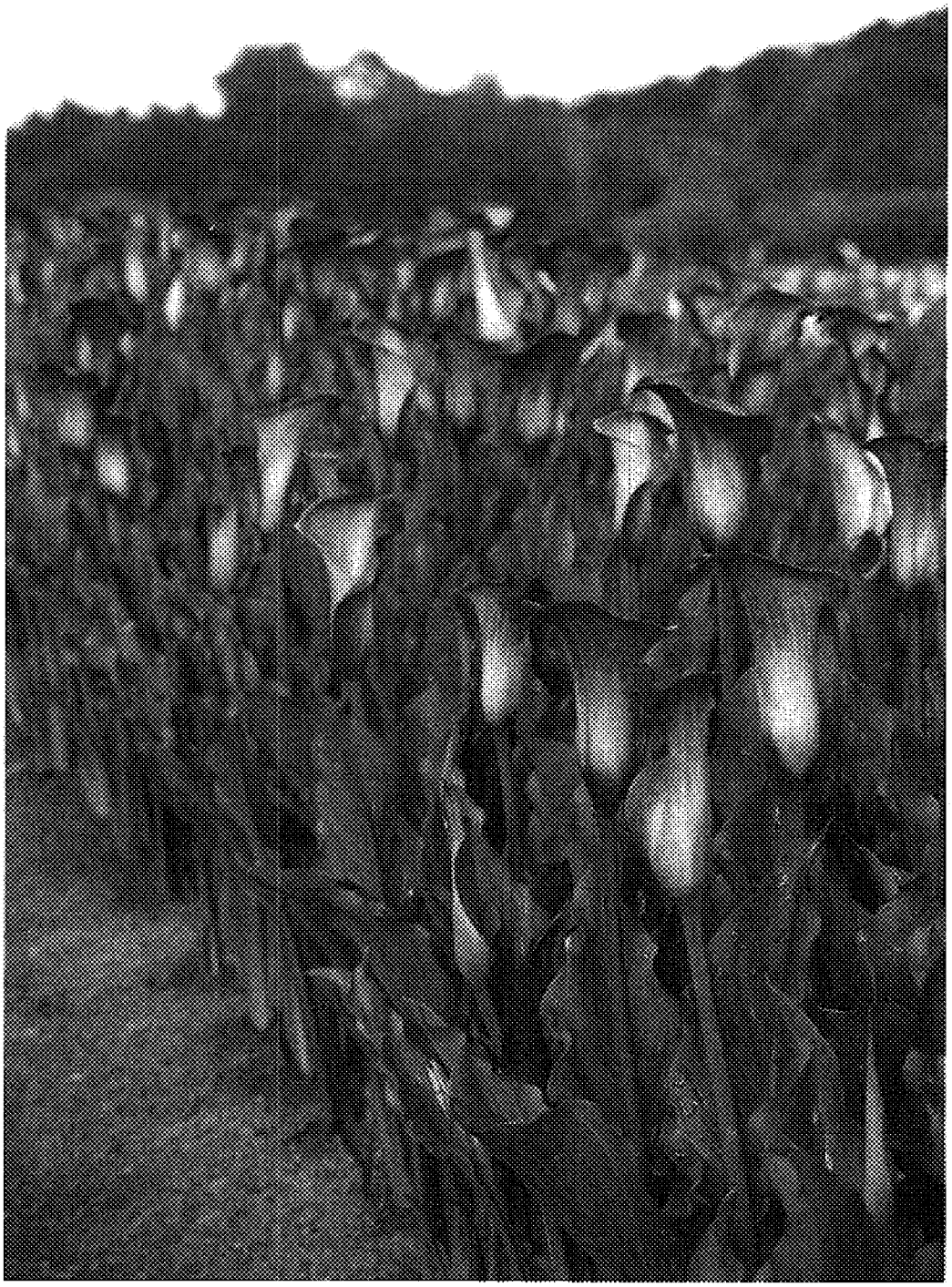
FIG. 2 illustrates a field of flowers of the new variety.

The following observations, measurements, and comparisons describe plants grown in New Zealand under conditions which approximate those generally used in horticulture practice. The field grown plants were 16 weeks into their third growing cycle when described. Color references are made to the R.H.S. Colour Chart of The Royal Horticultural Society of London, except where general color terms of ordinary significance are used.

THE PLANT

Size:
- *Height of the leaf canopy above the soil.*—400–900 mm; Average of 550 mm.
- *Height of top of flowers above the soil.*—400–900 mm; Average of 600 mm.
- *Diameter.*—150–400 mm; Average of 300 mm.
- *Form.*—Erect.

Number of flowers per tuber size:
- *Diameter of 3–4 cm.*—1–2 flowers.
- *Diameter of 4–5 cm.*—1–3 flowers.
- *Diameter of 5–6 cm.*—2–4 flowers.

Branches:
- *Character.*—Strong.
- *Color.*—147A.
- *Number.*—3–4 per plant.

Leaves:

*Size.*—Width: 80–150 mm; Average of 130 mm. Length: 150–300 mm; Average of 270 mm.

*Shape.*—Ovate-cordate.

*Apex.*—Apiculate to slightly rounded.

*Base.*—Rounded at the corners and smooth, but slightly ruffled along the base.

*Margin.*—Smooth, but slightly ruffled with a color of 53A on mature leaves, generally.

*Number per plant.*—10–15.

*Color.*—Upper surface: 147A. Lower surface: A combination of colors 146A and 146B.

*Spotting or mottling.*—Description: 8–40 maculations per leaf, ranging from 1 mm dots to 5 mm long×1 mm wide lines that follow the direction of the leaf venation. Appearance: Transparent, like a small window in the leaf. The mottling is caused by a small break in the green chlorophyll. There is no color.

*Veins.*—Configuration: Pinnate. Color: 144A.

*Surface quality.*—Leathery.

Petiole:

*Length.*—150–630 mm; Average of 300 mm.

*Diameter.*—8–13 mm.

*Color.*—144C with striations of 53A at the base of the petiole, changing to 144A up the length of the petiole.

Roots:

*Color.*—White.

*Branching.*—Moderate.

THE FLOWER

Spathe:

*Size.*—Length: 90–140 mm; Average of 120 mm. Width: 50–90 mm; Average of 75 mm.

*Color.*—Inner surface: A combination of colors 10B and 10C, having an overlay of a combination of colors 46A and 53A that intensifies at the rim of the spathe. Outer surface: Base of spathe is 144B with striations of 187A that changes to a combination of colors of 10B and 10C, having an overlay of a combination of colors of 46A and 53A that intensifies at the rim of the spathe. The tip of the spathe is 144B and 187A.

*Veins.*—Color: 187A at the base of the spathe, fading to 156C, then intensifying to 53A at the rim of the spathe. Configuration: Parallel.

*Shape.*—Overall: Cupped and rounded. Tip: Pointed and reflexed. Base: Cylindrical and widening distally. The overlap of the spathe is generally partially complete and flaring outwards.

Spadix:

*Size.*—Length: 40–45 mm. Diameter: 6–8 mm.

*Color.*—7A.

*Mature and immature reproductive organ color.*—Male: 7A. Female: 154D, with a hint of 53A speckling.

*Position relative to spathe.*—Upright.

Peduncle:

*Size.*—Length: 300–650 mm; Average of 500 mm. Diameter: 8–13 mm.

*Color.*—144A, with a combination of colors 46A and 53A striations streaked throughout.

Reproductive organs:

*Location of female organs.*—Basal position of the spadix (lower 40%); 10–25 female reproductive organs are located on the lower 10–15 mm.

*Location of male organs.*—Upper position of the spadix (upper 60%).

*Stamens.*—Not visible before pollen release.

*Pistil.*—Average number: 22. Length beyond perianth: 0.5 mm. Shape: Dome.

Flowering: Tubers planted in New Zealand begin to produce flowers 85 days after planting and continue to flower over a 20–30 day period.

Lastingness: Cut flowers last 5–14 days. On the plant stem, emergence to senescence is 19–22 weeks.

Fragrance: None.

Fruit:

*Size of individual seed pod.*—10–12 mm in diameter.

*Appearance of seed pod.*—Rounded and Smooth.

*Color of seed pod.*—144A fading at the base of the seed pod.

Seeds:

*Shape.*—Oval and rounded.

*Length.*—6–8 mm.

*Diameter.*—4–6 mm.

*Color.*—145C.

Disease resistance: Moderately high.

Pest resistance: High.

I claim:

1. A new and distinct cultivar of calla lily plant named 'Hawaii', as described and illustrated herein.

* * * * *

UNITED STATES PATENT AND TRADEMARK OFFICE

CERTIFICATE OF CORRECTION

PATENT NO. : PP 15,642 P3
DATED : March 5, 2005
INVENTOR(S) : Brljevich et al.

It is certified that error appears in the above-identified patent and that said Letters Patent is hereby corrected as shown below:

Column 4,
Line 35, under "Fruit", Color of seed pod, "fading at the base" should read -- fading to 144B at the base --.

Signed and Sealed this

Twentieth Day of September, 2005

JON W. DUDAS
*Director of the United States Patent and Trademark Office*